US007537779B2

(12) United States Patent
Modak et al.

(10) Patent No.: US 7,537,779 B2
(45) Date of Patent: *May 26, 2009

(54) ANTIMICROBIAL MEDICAL DEVICES

(75) Inventors: Shanta M. Modak, River Edge, NJ (US); Lester A. Sampath, Nyack, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1055 days.

This patent is subject to a terminal disclaimer.

(21) Appl. No.: 10/600,257

(22) Filed: Jun. 20, 2003

(65) Prior Publication Data
US 2004/0052831 A1 Mar. 18, 2004

Related U.S. Application Data

(63) Continuation of application No. PCT/US01/49205, filed on Dec. 21, 2001, which is a continuation-in-part of application No. 09/746,670, filed on Dec. 22, 2000, now Pat. No. 7,329,412.

(51) Int. Cl.
*A61F 2/02* (2006.01)
(52) U.S. Cl. .................................. 424/423
(58) Field of Classification Search .................. 424/423
See application file for complete search history.

(56) References Cited

U.S. PATENT DOCUMENTS

| 4,605,564 | A | 8/1986 | Kulla et al. | 427/2.3 |
|---|---|---|---|---|
| 4,723,950 | A | 2/1988 | Lee | 604/322 |
| 4,994,047 | A | 2/1991 | Walker et al. | 604/264 |
| 4,999,210 | A | 3/1991 | Solomon et al. | 427/2 |
| 5,013,306 | A | 5/1991 | Solomon et al. | 604/265 |
| 5,019,096 | A | 5/1991 | Fox, Jr. et al. | 600/36 |
| 5,033,488 | A | 7/1991 | Curtis et al. | 132/321 |
| 5,089,205 | A | 2/1992 | Huang et al. | 264/255 |
| 5,091,442 | A | 2/1992 | Milner | 523/122 |
| 5,102,401 | A | 4/1992 | Lambert et al. | 604/264 |
| 5,165,952 | A | 11/1992 | Solomon et al. | 427/2.25 |
| 5,180,605 | A | 1/1993 | Milner | 427/2.3 |
| 5,200,194 | A | 4/1993 | Edgren et al. | 424/473 |
| 5,209,251 | A | 5/1993 | Curtis et al. | 132/321 |
| 5,261,421 | A | 11/1993 | Milner | 128/898 |
| 5,335,373 | A | 8/1994 | Dresdner et al. | 2/161.7 |
| 5,357,636 | A | 10/1994 | Dresdner et al. | 2/161.7 |
| 5,420,197 | A | 5/1995 | Lorenz et al. | 525/54.3 |
| 5,451,424 | A | 9/1995 | Solomon et al. | 427/2.1 |
| 5,616,338 | A | 4/1997 | Fox, Jr. et al. | 424/423 |
| 5,707,366 | A * | 1/1998 | Solomon et al. | 604/265 |
| 5,772,640 | A | 6/1998 | Modak et al. | 604/265 |
| 6,083,208 | A | 7/2000 | Modak et al. | 604/265 |
| 6,106,505 | A | 8/2000 | Modak et al. | 604/265 |
| 6,224,579 | B1 | 5/2001 | Modak et al. | 604/265 |
| 6,261,271 | B1 * | 7/2001 | Solomon et al. | 604/265 |
| 6,626,873 | B1 | 9/2003 | Modak et al. | 604/265 |
| 6,706,024 | B2 * | 3/2004 | Modak et al. | 604/265 |
| 6,872,195 | B2 * | 3/2005 | Modak et al. | 604/265 |

FOREIGN PATENT DOCUMENTS

| EP | 0328421 | 8/1989 |
|---|---|---|
| EP | 0679271 | 7/1990 |
| EP | 0472413 | 8/1991 |
| EP | 0663212 | 5/1995 |
| JP | 11049625 | 2/1999 |
| WO | 9302717 | 2/1993 |
| WO | 9306881 | 4/1993 |
| WO | 9622114 | 7/1996 |
| WO | 9725085 | 7/1997 |
| WO | 0057933 | 10/2000 |

OTHER PUBLICATIONS

The Merck Index, An Encyclopedia of Chemicals, Drugs and Biologicals, Tenth Edition Merck & Co., Inc., Rahway, NJ, 1983, p. 1092.

Bach A, Bohrer H, Motsch J, Martin E, Geiss HK, Sonntag HG. Prevention of bacterial colonization of intravenous catheters by antiseptic impregnation of polyurethane polymers. J Antimicrob Chemother. May 1994;33(5):969-78.

Choi L, Choudhri AF, Pillarisetty VG, Sampath LA, Caraos L, Brunnert SR, Oz MC, Modak SM. Development of an infection-resistant LVAD driveline: a novel approach to the prevention of device-related infections. J Heart Lung Transplant. Nov. 1999;18(11):1103-10.

Tambe SM, Sampath L, Modak SM. In vitro evaluation of the risk of developing bacterial resistance to antiseptics and antibiotics used in medical devices. J Antimicrob Chemother. May 2001;47(5):589-98.

Kim CY, Kumar A, Sampath L, Sokol K, Modak S. Evaluation of an antimicrobial-impregnated continuous ambulatory peritoneal dialysis catheter for infection control in rats. Am J Kidney Dis. Jan. 2002;39(1):165-73.

(Continued)

*Primary Examiner*—Carlos A Azpuru
(74) *Attorney, Agent, or Firm*—Baker Botts L.L.P.

(57) ABSTRACT

The present invention provides for antimicrobial medical articles prepared by a method comprising treating a surface of the medical article with a solution consisting essentially of one or more solvents and a mixture of chlorhexidine free base and a water-soluble chlorhexidine salt, at a weight/weight ratio of between about 1:1 to about 1:5, wherein the combined concentration of chlorhexidine free base and a water-soluble salt of chlorhexidine is about 2% (w/v) or greater. In alternative embodiments, the antimicrobial medical articles may be treated with a similar solution in which the concentrations of chlorhexidine free base and a water-soluble salt of chlorhexidine are each about 0.20 percent (w/v). Other embodiments include those in which the solvent comprises methanol, or the treatment solution further comprises a silver salt, one or more organic acids, an anti-inflammatory agent, and a hydrogel.

64 Claims, No Drawings

OTHER PUBLICATIONS

Gaonkar TA, Sampath LA, Modak SM. Evaluation of the antimicrobial efficacy of urinary catheters impregnated with antiseptics in an in vitro urinary tract model. Infect Control Hosp Epidemiol. Jul. 2003;24(7):506-13.

On Apr. 17, 2000, which is prior to the Dec. 22, 2000 filing date of the present application (U.S. Appl. No. 09/746,670), a triple lumen catheter was sold by the licensee, Arrow Incorporated, in the United States. This catheter had an outer coating prepared using a solution containing three percent (3%) weight by volume (w/v) of chlorhexidine diacetate and 0.75 percent w/v silver sulfadiazine. The catheter had an inner lumen coating prepared using a solution containing the solvent ethanol, 0.75 percent (0.75%) w/v chlorhexidine free base, and 0.75 percent (0.75%) w/v chlorhexidine diacetate.

Printout from licensee Arrow's database, (Mar. 1999).

Mar. 8, 2000 Food and Drug Administration 510(k) Premarket Notification letter.

* cited by examiner

ANTIMICROBIAL MEDICAL DEVICES

CROSS REFERENCE TO RELATED APPLICATIONS

This application is a continuation of International Patent Application Ser. No. PCT/US01/49205, filed Dec. 21, 2001; which is a continuation-in-part of U.S. patent application Ser. No. 09/746,670, filed Dec. 22, 2000 now U.S. Pat No. 7,329, 412, the contents of which are hereby incorporated by reference in their entireties.

The present invention relates to medical devices treated with a solution comprising a combination of chlorhexidine free base and a water-soluble chlorhexidine salt, in a ratio that facilitates chlorhexidine uptake by the devices and hence improves antimicrobial effectiveness.

BACKGROUND OF THE INVENTION

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts and prosthetic devices, which not only are, themselves, in intimate contact with body tissues and fluids, but also create a portal of entry for pathogens.

Catheter related infections, especially blood stream infections, are associated with increased morbidity (10 to 20 percent), prolonged hospitalization (by a period having a mean of seven days), and increased medical costs (approximately $6,000 per hospitalization). According to a survey of intensive care units from 1986 through 1990 by the National Nosocomial Infection Surveillance System, the rate of catheter-related blood stream infections ranged from 2.1 to 30.2 per 1,000 catheter-days. Infections associated with central venous catheters have been reported to result from the transcutaneous migration of the pathogens from the insertion site with the eventual colonization of the catheter tip. In addition, intraluminal colonization has been suggested to result from contaminated hubs and infusates that contribute to catheter related blood stream infections. The longer the duration of catheterization, the greater the susceptibility to either luminal or outer surface colonization of catheters. Even for short term use of catheters, infections have been reported due to contamination of the insertion sites.

A number of methods for reducing the risk of infection have been developed which incorporate anti-infective agents into medical devices. Such devices desirably provide effective levels of anti-infective agent during the period that the device is being used. Sustained release may be problematic to achieve, in that a mechanism for dispensing anti-infective agent over a prolonged period of time may be required, and the incorporation of sufficient amounts of anti-infective agent may adversely affect the surface characteristics of the device. The difficulties encountered in providing effective antimicrobial protection increase with the development of drug-resistant pathogens.

One potential solution to these problems is the use of a synergistic combination of anti-infective agents that requires relatively low concentrations of individual anti-infective agents which may have differing patterns of bioavailability. For example, WO 97/25085 relates to medical devices comprising synergistic combinations of chlorhexidine and triclosan. U.S. Pat. Nos. 5,616,338 and 5,019,096 relate to infection resistant medical devices comprising synergistic combinations of a silver salt, a biguanide (such as chlorhexidine) and a polymeric component that forms a matrix to provide a sustained release of the silver salt and biguanide.

U.S. Pat. Nos. 5,165,952 and 5,451,424 relate to medical articles with chlorhexidine both coated on and bulk distributed throughout the medical articles. When chlorhexidine is bulk distributed it adversely affects certain characteristics of the device such as tensile strength, and the high temperatures needed for extension of plastics such as polyurethane may damage the chlorhexidine.

U.S. Pat. No. 5,089,205 relates to incorporation of chlorhexidine free base or one of its salts in a medical device such as a glove by both a distribution or dipping process.

Chlorhexidine is a broad spectrum antimicrobial agent and has been used as an antiseptic for several decades with minimal risk of developing resistant microbes. When relatively soluble chlorhexidine salts, such as chlorhexidine acetate, were used to impregnate catheters, the release was undesirably rapid. The duration of the antimicrobial efficacy of medical devices impregnated with chlorhexidine salts, such as chlorhexidine acetate, is short lived. Chlorhexidine free base is not soluble in water or alcohol and cannot be impregnated in sufficient amounts because of low solubility in a solvent system.

In contrast to the present invention, none of the above-cited references teach medical articles treated with a solution comprising a combination of chlorhexidine free base and a water-soluble chlorhexidine salt, at particular ratios, which provide improved antimicrobial effectiveness through an increased uptake of chlorhexidine into the medical device, increased retention of chlorhexidine in the medical device and prolonged release of chlorhexidine from the medical device, while utilizing relatively low levels of chlorhexidine.

SUMMARY OF THE INVENTION

The present invention relates to medical devices treated with a solution comprising one or more solvents and a combination of chlorhexidine free base and a water-soluble chlorhexidine salt, in a weight/weight ratio of between about 1:1 to about 1:5 (inclusive), preferably about 1:1 of chlorhexidine free base to chlorhexidine salt. The invention further relates to methods of preparing medical devices by exposing them, in whole or in part, to a solution comprising one or more solvents and the above-recited combinations of chlorhexidine free base and chlorhexidine salt.

This invention is based, at least in part, on the discovery that devices treated with combinations of chlorhexidine free base and a water-soluble chlorhexidine salt exhibit improved antimicrobial effectiveness due to increased uptake of chlorhexidine into the medical device, increased retention of chlorhexidine in the medical device, and prolonged release of chlorhexidine while utilizing relatively low levels of chlorhexidine, and, in certain non-limiting embodiments, in the absence of agents other than chlorhexidine. In particular, while it had been previously found that triclosan can be particularly useful when used in conjunction with chlorhexidine free base, it has been further discovered that medical articles having suitable antimicrobial properties may be prepared, according to the present invention, without the use of triclosan. Therefore, in particular embodiments, medical articles according to the present invention offer the advantage of preventing or inhibiting infection while avoiding undesirable adverse reactions to antimicrobial agents other than chlorhexidine by allergic individuals.

DETAILED DESCRIPTION OF THE INVENTION

The present invention provides for medical articles treated with a solution comprising one or more solvents and a combination of chlorhexidine free base ("CHX") and a water-soluble chlorhexidine salt, and further provides for methods of preparing medical devices by exposing the device, in whole or in part, to said solution.

While not being bound or limited by any particular theory, it is believed that the combination of CHX and water-soluble chlorhexidine salt forms a soluble complex. This would explain the increased uptake of chlorhexidine into the medical device, increased retention of chlorhexidine in the medical device, and increased sustained release of chlorhexidine from the medical device while utilizing relatively low levels of chlorhexidine in the absence of agents other than chlorhexidine.

The following are definitions of terms used herein unless otherwise indicated:

Water soluble chlorhexidine salts have a solubility of at least about 2.0 grams per 100 ml in water at 20° C. Examples of water soluble chlorhexidine salts include chlorhexidine diacetate (also referred to herein as chlorhexidine acetate, or "CHA") and chlorhexidine digluconate (or "CHG") with CHA being preferred.

The terms "medical article" and "medical device" are used interchangeably herein. Medical articles that may be treated according to the invention are either fabricated from and/or coated or treated with biomedical polymer (and hence may be referred to as "polymeric medical articles") and include, but are not limited to, catheters including urinary catheters and vascular catheters (e.g., peripheral and central vascular catheters), wound drainage tubes, arterial grafts, soft tissue patches (such as polytetrafluoroethylene (PTFE) soft tissue patches), gloves, condoms, shunts, stents, tracheal catheters, wound dressings, sutures, guide wires and prosthetic devices (e.g., heart valves and LVADs). Medical articles that may be treated according to the invention include soft tissue patches made of expanded PTFE ("e-PTFE"), which is commercially available from W.L. Gore under the trade name. Gore-Tex. Polymeric medical articles that may be treated according to the invention also include biodegradable polymers (such as polylactic acid (PLA), polyglycolic acid (PGA) and polycaprolactone (PCL)) with PCL being preferred. Vascular catheters which may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters. The present invention may be further applied to medical articles that have been prepared according to U.S. Pat. Nos. 5,616,338 and 5,019,096 by Fox, Jr. et al. and U.S. Pat. No. 5,772,640 by Modak et al.

The term "hydrophilic polymeric medical article" is a medical article fabricated from a hydrophilic polymer. As used herein, "hydrophilic polymer" refers to polymers that have a water absorption greater than 0.6 percent by weight (and, in preferred embodiments, less than 2 percent by weight; as measured by a 24 hour immersion in distilled water, as described in ASTM Designation D570-81) including, but not limited to biomedical polyurethanes (e.g., ether-based polyurethanes and ester-based polyurethanes, as set forth in Baker, 1987, in *Controlled Release of Biologically Active Agents*, John Wiley and Sons, pp. 175-177 and Lelah and Cooper, 1986, *Polyurethanes in Medicine*, CRC Press, Inc., Fla. pp. 57-67; polyurethanes comprising substantially aliphatic backbones such as Tecoflex™ 93A; polyurethanes comprising substantially aromatic backbones such as Tecothane™; and Pellethane™), polylactic acid, polyglycolic acid, natural rubber latex, and gauze or water-absorbent fabric, including cotton gauze and silk suture material.

The term "hydrophobic polymeric medical article" is a medical article fabricated from a hydrophobic polymer. As used herein, "hydrophobic polymer" refers to a polymer that has a water absorption of less than 0.6% (w/w) and includes, but is not limited to, silicone polymers such as biomedical silicones (e.g., Silastic Type A) or elastomers (e.g., as set forth in Baker, 1987, in *Controlled Release of Biologically Active Agents*, John Wiley and Sons, pp. 156-162), Dacron, PTFE (also "Teflon"), expanded PTFE, polyvinyl chloride (PVC), cellulose acetate, polycarbonate, and copolymers such as silicone-polyurethane copolymers (e.g., PTUE 203 and PTUE 205 polyurethane-silicone interpenetrating polymer).

The terms "treat", "treated", "treating", etc., as used herein, refer to coating, impregnating, or coating and impregnating a medical article with anti-infective agent. Medical articles are "treated" by exposing them, for an effective period of time, to a treatment solution, where an "effective period of time" is that period of time sufficient to introduce anti-infective qualities of the anti-infective agent to the articles. Medical articles may be dipped, soaked, or otherwise have a surface coated. The term "dipped" suggests briefer exposure to the treatment solution relative to "soaking," and preferably is for a period of time less than fifteen minutes.

Percentages recited herein refer to weight/volume (w/v), except as indicated otherwise (e.g., volume/volume or "v/v").

The term "CFU" means colony forming unit.

The term "about" indicates a variation within 20 percent.

The present invention provides for medical articles treated with a solution comprising one or more solvents and a combination of CHX and a water-soluble chlorhexidine salt, in a weight/weight ratio of between about 1:1 and 1:5, preferably about 1:1. Such medical articles include hydrophilic polymeric medical articles as well as hydrophobic polymeric medical articles fabricated from and/or coated or treated with such a biomedical polymer. In addition, the present invention may be applied to medical articles that have been prepared according to U.S. Pat. Nos. 5,616,338 and 5,019,096 by Fox, Jr. et al. and U.S. Pat. No. 5,772,640 by Modak et al. Such one or more solvents may be selected from the group consisting of water, reagent alcohol, and tetrahydrofuran ("THF"), dimethylsulfoxide, dimethylformamide, N-methyl-2-pyrrolidone, and mixtures thereof.

In a specific non-limiting embodiment, the treatment solution comprises CHX-CHA in a weight/weight ratio between about 1:1 and about 1:5, preferably about 1:1 of CHX to CHA.

The present invention further provides, in a non-limiting embodiment, for methods of preparing medical devices by treating the device, in whole or in part, with a solution comprising one or more solvents and a complex formed by synergistic combinations of chlorhexidine free base and chlorhexidine acetate.

In non-limiting embodiments, medical articles may be treated with a solution comprising the steps of (i) placing the medical article in a solution comprising (a) a solvent selected from the group consisting of water, reagent alcohol, THF, dimethylsulfoxide, dimethylformamide, N-methyl-2-pyrrolidone, and mixtures thereof and (b) a mixture of CHX and a water-soluble chlorhexidine salt, preferably CHA, preferably in a weight/weight ratio of between about 1:1 and about 1:5; (ii) soaking the medical article in the solution for an effective period of time to allow the medical article to swell and to incorporate the anti-infective agents; (iii) removing the medical article from the solution; and (iv) drying the medical article.

Medical articles prepared according to the invention may be treated on an external surface, internal surface, or both. For example, and not by way of limitation, where the medical article is a catheter having a lumen, the internal (i.e., luminal) surface and/or external surface of the catheter may be treated together or separately according to the invention. An open-ended catheter may be placed in a treatment solution such that the internal and external surfaces are exposed to the treatment solution. Alternatively, the ends of the catheter may be sealed before being placed in the treatment solution so that only the external surface is exposed to the treatment solution. Alternatively, only the internal surface may be exposed to the treatment solution if the solution is pushed, pulled or allowed to pass through and/or fill the lumen without immersing the catheter in the treatment solution.

In specific non-limiting embodiments, a catheter having a lumen may be treated with a solution comprising the steps of (i) exposing the lumen of the catheter to a solution comprising (a) a solvent selected from the group consisting of water, alcohol, THF, dimethylsulfoxide, dimethylformamide, N-methyl-2-pyrrolidone, and mixtures thereof and (b) a mixture of CHX and a water-soluble chlorhexidine salt, preferably CHA, preferably in a molar ratio of between about 1:1 and about 1:5; (ii) filling the lumen of the catheter with the solution by pushing, pulling, or allowing passage of the solution into the lumen for an effective period of time to allow the material surrounding the lumen of the catheter to swell and to incorporate the chlorhexidine; (iii) removing the solution from the lumen of the catheter; and (iv) drying the catheter.

In the foregoing methods, the duration of exposure of the medical article or portion thereof to the treatment solution may preferably, but not by limitation, be ten seconds to one hour. The duration of exposure of the lumen of a catheter may preferably, but not by limitation, be ten seconds to two minutes. Longer periods of exposure may be used provided that undesirable deterioration of the medical article does not occur.

The treatment solutions may optionally further comprise (i) an organic acid, at a concentration of between about 0.1 and about 5 percent, preferably between about 0.1 and about 2 percent; (ii) an anti-inflammatory agent, at a concentration of between about 0.1 and about 5 percent, preferably between about 0.1 and about 1 percent; and/or (iii) a hydrogel at a concentration of between about 0.5 to about 10 percent, preferably between about 1 and about 5 percent, and/or a polymer at a concentration of between about 0.1 and about 6 percent, preferably between about 0.1 and about 4 percent.

WORKING EXAMPLES

The following methods were used in performing experiments discussed in the following examples, unless indicated otherwise:

Method of Treatment of a Medical Article with Solution. The medical article was treated by exposing the entire medical article, or a portion thereof, to a solution containing CHA alone, CHX alone or the CHX-CHA combination in various amounts in a solvent system. The medical article, or a portion thereof, was exposed by soaking the article in the solution for 100 seconds before removing the article from the solution. For articles, such as catheters, having an internal lumen, the solution was pushed into the lumen and allowed to remain for 100 seconds before removal.

Method of Determining Drug Uptake. The amount of drug uptake into the treated polymeric medical articles was determined using a spectrophotometric method after extraction in alcohol.

Method of Determining Long Term Antimicrobial Efficacy in Catheter Lumen. In order to determine the duration of antimicrobial efficacy in catheter lumens exposed to treatment solutions, catheters were perfused for 7 days using the following continuous perfusion model. The distal lumens of catheters were connected to a peristaltic pump in a closed loop, wherein 1.5 L of 10% (v/v) trypticase soy broth in saline was constantly perfused by recycling it through each catheter lumen at a rate of 83 ml/hr for 7 days. On the eighth day the catheters were disconnected and used for evaluation of bacterial adherence.

Method of Evaluating Microbial Adherence to a Catheter Lumen. After perfusion of catheters for 7 days as set forth above, the distal lumens of each catheter were filled with a $10^8$ CFU/ml culture of bacteria or yeast. In the case of exposure to E. aerogenes, P. aeruginosa and C. albicans, cultures containing $10^6$ CFU/ml were used. The ends of the catheters were heat sealed and the catheters were incubated for 24 hours in an orbital shaker at 37° C. After 24 hours, the lock cultures were collected from the lumen and subcultured after serial dilution using agent inactivating media. The outer surface of the whole catheter was sterilized by wiping the outer surface with an alcohol swab. Thereafter, the lumens were flushed with 20 ml trypticase soy broth to remove non-adherent bacteria. The body of the catheters were subdivided into 2 cm segments, which were further cut into 2 mm subsegments. The subsegments were placed in 4.0 ml agent inactivating media and sonicated in a 4° C. water bath using an Astrasan Sonicator (Model 9T) at 60 KHertz. Thereafter, 0.5 ml of the extract was then subcultured on a trypticase soy agar plate and incubated at 37° C. for 24 hours. Colony counts were then determined.

Method of Evaluating Bacterial Adherence to PTFE Soft Tissue Patch Disks. Polytetrafluoroethylene (PTFE) disks were soaked and agitated in 3.0 ml of media containing 50% (v/v) bovine adult serum and 50% (v/v) trypticase soy broth. The media was changed on days 1, 2 and 4. On the fourth day, $10^5$ CFU/ml of bacteria was added to the media. On the fifth day, the disks were removed, rinsed and rolled on drug inactivating agar. The plates were then incubated for 24 hours at 37° C. Colony counts were determined thereafter.

Method of Determining Zones of Inhibition. Zones of inhibition were measured by seeding a specified amount of bacteria onto a trypticase soy agar plate. Then, three units of a specified amount of medical article were placed on the plate. The plates were incubated at 37° C. for 24 hours. The zones of inhibition were then measured for Day 1. To measure the zones of inhibition on Day 2 and subsequent days, the units of medical article were transferred onto a fresh plate of similarly prepared agar, incubated at 37° C. for 24 hours and colony-free zones were measured.

1. EXAMPLE

Polyurethane Central Venous Catheters

Polyurethane central venous catheters, which are hydrophilic polymeric medical articles, were separated into three otherwise identical groups of catheters and separately treated with a solution that either (i) contained no antimicrobial agents; (ii) contained CHA alone, or (iii) contained a combination of CHX and CHA ("CHX-CHA") in accordance with the present invention. In particular, the luminal surfaces of the catheters were separately treated with one of the following solutions:

(1) a solvent system of 80% (v/v) reagent alcohol and 20% (v/v) THF with no antimicrobial agents;

(2) 2.4% CHA in a solvent system of 80% (v/v) reagent alcohol and 20% (v/v) THF; and (3) 1.2% CHX and 1.2% CHA in a solvent system of 80% (v/v) reagent alcohol and 20% (v/v) THF.

The solution was exposed to the luminal surface of the catheter by pushing the solution into the lumen and allowing the solution to remain in the lumen for 100 seconds. Thereafter, the solution was removed, and the distal lumens of the catheters were connected to a peristaltic pump in a closed loop, wherein 1.5 L of 10% trypticase soy broth in saline was constantly perfused by recycling it through each catheter lumen at a rate of 83 ml/hr for 7 days, according to the continuous perfusion method discussed above. On the eighth day the catheters were disconnected and the ability of bacteria to adhere to the lumens was tested as follows.

The distal lumens of each of the three groups of catheters were separately filled with $8\times10^8$ CFU/ml culture of *S. epidermidis*. The ends of the catheters were heat sealed and the catheters were incubated for 24 hours in an orbital shaker at 37° C. After 24 hours, the lock cultures were collected from the lumen and subcultured after serial dilution using agent inactivating media. The outer, surface of the whole catheter was sterilized by wiping the outer surface with an alcohol swab. Thereafter, the lumens were flushed with 20 ml trypticase soy broth to remove non-adherent bacteria. The bodies of the catheters were subdivided into 2 cm segments, which were further cut into 2 mm subsegments. The subsegments were placed in 4.0 ml agent inactivating media and sonicated in a 4° C. water bath using an Astrasan Sonicator (Model 9T) at 60 KHertz. Thereafter, 0.5 ml of the extract was then subcultured on a trypticase soy agar plate and incubated at 37° C. for 24 hours. Colony counts were then determined and are shown below in Table 1.

TABLE 1

| Solution | Bacterial Adherence of *S. epidermidis* (CFU/cm) |
|---|---|
| 80% (v/v) reagent alcohol + 20% (v/v) THF | $2.2 \times 10^4$ |
| 2.4% CHA in 80% (v/v) reagent alcohol + 20% (v/v) THF | $3 \times 10^2$ |
| 1.2% CHX + 1.2% CHA in 80% (v/v) reagent alcohol + 20% (v/v) THF | 2 |

The luminal surfaces of catheters were also tested according to the above described techniques to evaluate the adherence of a wide variety of organisms. The luminal surfaces of catheters were separately treated with the following solutions:

(1) a solvent system of 80% (v/v) reagent alcohol and 20% (v/v) THF with no antimicrobial agents; and (2) 1.2% CHX and 1.2% CHA in a solvent system of 80% (v/v) reagent alcohol and 20% (v/v) THF.

The luminal surfaces were exposed to the respective solutions for 100 seconds. Thereafter, the solutions were removed, and the lumens were perfused according to the continuous perfusion method discussed above.

On the eighth day, the catheters were disconnected and susceptibility to microbial adherence was evaluated. The distal lumens of each group of catheters were separately filled with the following amounts of bacteria (*S. aureus*, *P. aeruginosa*, and *Enterobacter*) or yeast (*C. albicans*):

(1) $8\times10^8$ CFU/ml culture of *S. aureus*;

(2) $8\times10^6$ CFU/ml culture of *P. aeruginosa*;

(3) $8\times10^8$ CFU/ml culture of *Enterobacter*; and (4) $8\times10^6$ CFU/ml culture of *C. albicans*.

The four subgroups of lumens were prepared for evaluating microbial adherence to the catheter lumens as described above. The ends of the catheters were heat sealed, incubated, subcultured, externally sterilized, flushed, subdivided, placed in inactivating media and sonicated according to the techniques set forth supra. Thereafter, 0.5 ml of the extract was subcultured, incubated and examined to determine the colony counts. The results are shown below in Table 2.

TABLE 2

| Solution | Adherence of *S. aureus* (CFU/cm) | Adherence of *P. aeruginosa* (CFU/cm) | Adherence of Enterobacter (CFU/cm) | Adherence of *C. albicans* (CFU/cm) |
|---|---|---|---|---|
| 80% (v/v) reagent alcohol + 20% (v/v) THF | $1.3 \times 10^4$ | $>10^5$ | $>10^5$ | $1.7 \times 10^4$ |
| 1.2% CHX + 1.2% CHA in 80% (v/v) reagent alcohol + 20% (v/v) THF | 3 | 9 | 2 | 26 |

The results shown in Table 1 demonstrate the synergistic antimicrobial effect of treating a polyurethane central venous catheter lumen with a solution comprising the mixture of CHX and CHA. Table 2 shows that articles treated with CHX and CHA exhibit an increased effectiveness across a wide variety of organisms by decreasing luminal adherence substantially more than articles treated with no antimicrobial agents.

In a further study, the luminal surface of three groups of otherwise identical polyurethane central venous catheters were separately treated with one of the following three solutions:

(1) 2% CHA in a solvent system of 80% (v/v) ethanol and 20% (v/v) THF;

(2) 0.625% CHX and 1.375% CHA in a solvent system of 80% (v/v) ethanol plus 20% (v/v) THF; and (3) 1% CHX and 1% CHA in a solvent system of 80% (v/v) ethanol plus 20% (v/v) THF.

The solution was pushed into the lumen and allowed to remain for 100 seconds.

The amount of uptake of chlorhexidine in the catheters was determined using a spectrophotometric method after extraction with alcohol.

In order to determine the amount of drug retention and antimicrobial efficacy, the catheters were perfused for 6 days with 1.500 L of saline per day. The treated catheters were then studied on Day 1 and Day 6 after perfusion to determine the amount of drug retention. The chlorhexidine in the catheter after perfusion was determined using a spectrophotometric method after extraction with alcohol. The antibacterial activity was measured on Day 6 after perfusion by counting the CFU/cm of *S. epidermidis*. Table 3 shows results of the uptake, drug retention and antibacterial activity of the treated catheters.

TABLE 3

| Solution | Uptake (μg/cm) | Retention of Drug (μg/cm) Day 1 | Retention of Drug (μg/cm) Day 6 | Antibacterial Activity (CFU/cm) *S. epidermidis* Day 6 |
|---|---|---|---|---|
| 2% CHA in 80% (v/v) Ethanol + 20% (v/v) THF | 44 | 34 | 8 | $10^2$ |
| 0.625% CHX + 1.375% CHA in 80% (v/v) Ethanol + 20% v/v THF | 70 | 43 | 22 | 0 |
| 1% CHX + 1% CHA in | 80 | 45 | 26 | 0 |

TABLE 3-continued

| Solution | Uptake (μg/cm) | Retention of Drug (μg/cm) Day 1 | Day 6 | Antibacterial Activity (CFU/cm) S. epidermidis Day 6 |
|---|---|---|---|---|
| 80% (v/v) Ethanol + 20% (v/v) THF | | | | |

These results demonstrate the synergistic antimicrobial effect of treating a polyurethane central venous catheter lumen with a solution comprising a mixture of CHX and CHA.

2. EXAMPLE

Urinary Catheters

Hydrophilic urinary catheters were separated into two otherwise identical groups, and the whole catheters (i.e., external and luminal surfaces of the catheter) were treated with a solution containing either:
(1) 4% CHA in a solvent system of 85% (v/v) THF and 15% (v/v) methanol; or
(2) 2% CHX plus 2% CHA in a solvent system of 85% (v/v) THF and 15% (v/v) methanol.

The catheters of each group were soaked in the respective solution for 30 minutes to one hour. Thereafter, the catheters were removed from the solution.

The amount of uptake of chlorhexidine was determined using a spectrophotometric method after extraction with alcohol, which results are shown below in Table 4.

The two groups of catheters were separately exposed to cultures of *P. aeruginosa* and *C. albicans* in order to study the antimicrobial efficacy of the medical article. Trypticase soy agar plates were seeded with 0.3 ml of $10^8$ CFU/ml of *P. aeruginosa* and *C. albicans*, respectively. Thereafter, a 0.5 cm length of urinary catheter was placed on each plate with three units per plate. The plates were then incubated for 24 hours at 37° C. After 24 hours, the zones of inhibition were measured, for Day 1. To measure the zones of inhibition for Day 2 to Day 6, the process was repeated upon transferring the units to fresh agar plates similarly prepared. The results are shown in Table 4.

These results demonstrate the synergistic antimicrobial effect of treating the urinary catheters with a solution comprising a mixture of CHX and CHA.

3. EXAMPLE

PTFE Soft Tissue Patches

Disks cut from PTFE soft tissue patches, which are hydrophobic polymeric medical articles, were treated with a solution that contained CHA alone and a solution that contained a CHX-CHA complex in accordance with the present invention. Groups of disks having a 1 mm thickness were treated for one hour with one of the following solutions:
(1) 0.4% CHA in a solvent system of 70% (v/v) THF and 30% (v/v) methanol; or
(2) 0.2% CHX and 0.2% CHA in a solvent system of 70% (v/v) THF and 30% (v/v) methanol.

The amount of uptake of chlorhexidine in the PTFE disks was determined using a spectrophotometric method after extraction with alcohol, and the results are shown below in Table 5.

The two groups of disks were separately exposed to cultures of *P. aeruginosa* and *S. epidermidis* in order to study their antimicrobial efficacy. Trypticase soy agar plates were seeded with 0.3 ml of $10^8$ CFU/ml of *P. aeruginosa* and *C. albicans*, respectively. Thereafter, 0.5 cm diameter disks were placed on each plate with three units per plate. The plates were then incubated for 24 hours at 37° C. After 24 hours, the zones of inhibition were measured for Day 1. The process was repeated upon transferring the disks to fresh agar plates similarly prepared for Day 2 to Day 6. The zones of inhibition are shown in Table 5.

TABLE 5

| Solution | Uptake (μg/cm) | Antimicrobial Efficacy (Zone of Inhibition (mm)) P. aeruginosa Day | | | | Antimicrobial Efficacy (Zone of Inhibition (mm)) S. epidermidis Day | | | |
|---|---|---|---|---|---|---|---|---|---|
| | | 1 | 2 | 3 | 4 | 1 | 2 | 3 | 4 |
| 0.4% CHA in 70% (v/v) THF + | 450 | 8 | 5 | 0 | 0 | 12 | 10 | 9 | 9 |

TABLE 4

| Solution | Uptake (μg/cm) | Antimicrobial Efficacy (Zone of Inhibition (mm)) P. aeruginosa Day | | | | | | Antimicrobial Efficacy (Zone of Inhibition (mm)) C. albicans Day | | | | | |
|---|---|---|---|---|---|---|---|---|---|---|---|---|---|
| | | 1 | 2 | 3 | 4 | 5 | 6 | 1 | 2 | 3 | 4 | 5 | 6 |
| 4% CHA in 85% (v/v) THF + 15% (v/v) Methanol | 123 | 15 | 11 | 10 | 9 | 0 | 0 | 11 | 9 | 0 | 0 | 0 | 0 |
| 2% CHX + 2% CHA in 85% (v/v) THF + 15% (v/v) Methanol | 380 | 16 | 13 | 11 | 10 | 10 | 10 | 12 | 11 | 11 | 10 | 9 | 6 |

TABLE 5-continued

| Solution | Uptake (µg/cm) | Antimicrobial Efficacy (Zone of Inhibition (mm)) P. aeruginosa Day | | | | Antimicrobial Efficacy (Zone of Inhibition (mm)) S. epidermidis Day | | | |
|---|---|---|---|---|---|---|---|---|---|
| | | 1 | 2 | 3 | 4 | 1 | 2 | 3 | 4 |
| 30% (v/v) Methanol 0.2% CHX + 0.2% CHA in 70% (v/v) THF + 30% (v/v) Methanol | 840 | 12 | 8 | 8 | 7 | 15 | 13 | 12 | 11 |

These results demonstrate the synergistic effect of treating PTFE soft tissue patches with a solution comprising a mixture of CHX and CHA.

Bacterial adherence on PTFE soft tissue patch disks treated with CHA alone, CHX alone, or a mixture of CHA and CHX were studied. 2 mm thick disks were separated into four groups and separately treated with one of the following solutions:

(1) a solvent system of 70% (v/v) THF and 30% (v/v) methanol with no antimicrobial;

(2) 0.4% CHA in a solvent system of 70% (v/v) THF and 30% (v/v) methanol;

(3) 0.4% CHX in a solvent system of 70% (v/v) THF and 30% (v/v) methanol; and (4) 0.2% CHX and 0.2% CHA in a solvent system of 70% (v/v) THF and 30% (v/v) methanol.

In order to determine the bacterial adherence to the PTFE, three disks of 1 cm diameter from patches in each treatment group were soaked and agitated in 3.0 ml of media containing 50% (v/v) bovine adult serum and 50% (v/v) trypticase soy broth. The media was changed on days 1, 2 and 4. On the fourth day, $10^5$ CFU/ml of S. aureus was added to the media. On the fifth day after agitation in media, the disks were removed, rinsed and rolled on to plates of drug inactivation agar. The plates were then incubated for 24 hours at 37° C. Thereafter, the colony counts were determined, and the amount of antimicrobial present in the disks was determined by extracting the antimicrobial from the disk with alcohol, followed by spectrophotometric measurement. The results are shown in Table 6.

TABLE 6

| Solution | Drug levels (µg/disk) | Bacterial Adherence of S. aureus (CFU/cm) Day 5 |
|---|---|---|
| 70% (v/v) THF + 30% (v/v) methanol | 0 | >$10^5$ |
| 0.4% CHA In 70% (v/v) THF + 30% (v/v) methanol | 264 | 8 × $10^2$ |
| 0.4% CHX in 70% (v/v) THF + 30% (v/v) methanol | 361 | 1 × $10^2$ |
| 0.2% CHA + 0.2% CHX in 70% (v/v) THF + 30% (v/v) methanol | 360 | 60 |

These results demonstrate the synergistic effect of treating PTFE soft tissue patches with a solution comprising a mixture of CHX and CHA.

4. EXAMPLE

Polyurethane Central Venous Catheters

In a further study of the drug retention properties of polyurethane central venous catheters treated with a solution containing a combination of CHX and CHA ("CHX-CHA") in accordance with the present invention, the outer surfaces of otherwise identical catheters were treated with (i) CHA and silver sulfadiazine ("AgSD"), and (ii) CHX-CHA and AgSD. In particular, the ends of the catheters were sealed and the outer surfaces of the catheters were impregnated by dipping the closed catheters for 5 seconds in one of the following solutions:

(1) 3.5% CHA+0.75% AgSD+3% 93A+1% 60D;

(2) 2% CHA+1.5% CHX+0.75% AgSD+3% 93A+1% 60D; and (3) 2% CHA+1.5% CHX+0.75% AgSD+2.5% 93A+2% 60D.

The treated catheters were then tested for drug retention at various times using an in vitro agar tract model (method A) or an in vivo rat subcutaneous model (method B).

Method A: The bodies of the treated catheters were subdivided into 4 cm segments and implanted into 12.5 ml culture medium of 0.5 agar+0.03 trypticase soy broth ("TSB")+20% bovine adult serum ("BAS")+0.5% Parmalat in a 15 ml culture tube. The catheter segments were transferred to fresh medium on day 8, 26, 33, and 40 to simulate in vivo drug clearance. The drug levels were determined at day 8, 14, 22 and 50.

Method B: The bodies of the treated catheters were subdivided into 4 cm segments and implanted under the skin of the test rats. The catheter segments were removed at day 8, 14 and 22 for determination of drug level.

In order to determine the drug level, 1 cm segments of the catheters were extracted with 2 ml dichloromethane. Thereafter, 4 ml of 50% reagent alcohol were added to remove the chlorhexidine from the dichloromethane layer. The results were read spectrophotometrically at 251 nm to determine the concentrations. The drug levels in, measured in µg/cm, were determined over time and are shown for those catheters tested under method A in Table 7 below and for those catheters tested under method B in Table 8 below.

TABLE 7

| SOLUTION | CHLORHEXIDINE RETENTION (µg/cm) Method A (in vitro) | | | | |
|---|---|---|---|---|---|
| | Day 0 | Day 7 | Day 14 | Day 22 | Day 50 |
| 3.5% CHA + 0.75% AgSD + 3% 93A + 1% 60D | 431 | 173 | 123 | 96 | 89 |
| 2% CHA + 1.5% CHX + 0.75% AgSD + 3% 93A + 1% 60D | 426 | 256 | 214 | 161 | 113 |
| 2% CHA + 1.5% CHX + 0.75% AgSD + 2.5% 93A + 2% 60D | 444 | 328 | 257 | 236 | 158 |

TABLE 8

| SOLUTION | CHLORHEXIDINE RETENTION (μg/cm) Method B (in vivo) | | | |
|---|---|---|---|---|
| | Day 0 | Day 7 | Day 14 | Day 22 |
| 3.5% CHA + 0.75% AgSD + 3% 93A + 1% 60D | 431 | 145 | 144 | 103 |
| 2% CHA + 1.5% CHX + 0.75% AgSD + 3% 93A + 1% 60D | 426 | 301 | 259 | 195 |
| 2% CHA + 1.5% CHX + 0.75% AgSD + 2.5% 93A + 2% 60D | 444 | 345 | 308 | 263 |

These results demonstrate that the drug levels of catheters treated with CHX-CHA and AgSD have a significantly higher drug retention under either testing method than catheters treated with similar drug levels of CHA alone with AgSD. Further, it is observed that changing the polymer component of the treatment solution containing CHX-CHA from 3% 93A+1% 60D to 2.5% 93A+2% 60D enhanced the effectiveness of the drug retention.

Catheters were prepared for evaluating bacterial adherence to the outer surfaces of each of the three groups of catheters described above. Catheters from each of the three groups were separately implanted according to either the agar tract model (method A) or the rat subcutaneous model (method B) described above and infected with *Staphylococcus aureus* at various time intervals. Bacterial adherence was determined 7 days after infection. Under method A, the medium was changed at day 8, 26, 33 and 40, as stated previously, and infected at day 14, 29 and 44 with 20 μl of a $1 \times 10^7$ cfu/ml of *S. aureus* suspension. Under method B, each catheter segment was infected with a 25 μl of a $1 \times 10^8$ cfu/ml of *S. aureus* suspension on day 21. The body of the catheters were subdivided into 1 cm sub segments, placed in a 4.0 ml drug inactivating media, and sonicated in a 4° C. water bath using an Astrasan Sonicator (Model 9T) at 60 KHertz. Thereafter, 0.5 ml of the extract was then subcultured on a trypticase soy agar plate and incubated at 37° for 24 hours. Colony counts were then determined. The results of the colony counts under methods A and B are shown in Table 9 by day of infection.

TABLE 9

| SOLUTION | BACTERIAL ADHERENCE (cfu/cm) (*S. aureus*) | | | | |
|---|---|---|---|---|---|
| | Method A (in vitro) | | | Method B (in vivo) | |
| | Day 14 | Day 21 | Day 44 | Day 14 | Day 21 |
| 3.5% CHA + 0.75% AgSD + 3% 93A + 1% 60D | 3 | 11 | 390 | 0 | 10 |
| 2% CHA + 1.5% CHX + 0.75% AgSD + 3% 93A + 1% 60D | 0 | 6 | 2 | 0 | 6 |
| 2% CHA + 1.5% CHX + 0.75% AgSD + 2.5% 93A + 2% 60D | 0 | 7 | 59 | 0 | 9 |

These results demonstrate that under methods A and B all of the groups of catheters were effective up to the 21st day post implantation. However, at 44 days post infection the catheters treated with CHA-CHX and AgSD in accordance with the present invention had significantly lower colonization than the catheters with similar drug levels of CHA and AgSD without combination with CHX. Further, it is observed that changing the polymer component of the treatment solution containing CHX-CHA from 2.5% 93A+2% 60D to 3% 93A+1% 60D resulted in even lower colonization.

5. EXAMPLE

Expanded PTFE Soft Tissue Patches

In a further study of the drug retention properties and bacterial adherence of soft tissue patches, disks cut from expanded PTFE soft tissue patches were separately treated with one of the following solutions containing the specified amounts of CHA, CHX-CHA complex in accordance with the present invention, silver carbonate ("$Ag_2CO_3$"), triclosan ("TC") and/or polycaprolactone ("PCL") in a solvent system containing ammonium hydroxide ("$NH_4OH$"), methyl alcohol ("MetOH"), and tetrahydrofuran ("THF"):

(1) 0.4% CHA+0.2% $Ag_2CO_3$ in 20% (v/v) $NH_4OH$+10% (v/v) MetOH+70% (v/v) THF;

(2) 0.4% CHA+0.1% $Ag_2CO_3$+1% PCL (w/v) in 10% (v/v) NH4OH+10% (v/v) MetOH+80% (v/v) THF;

(3) 0.2% CHA+0.2% CHX+0.2% $Ag_2CO_3$ in 10% (v/v) $NH_4OH$+10% (v/v) MetOH+80% (v/v) THF;

(4) 0.2% CHA+0.2% CHX+0.1% $Ag_2CO_3$+1% (w/v) PCL in 10% (v/v) $NH_4OH$+10% (v/v) MetOH+80% (v/v) THF;

(5) 0.2% CHA+0.2% TC+0.2% $Ag_2CO_3$ in 20% (v/v) $NH_4OH$+10% (v/v) MetOH+70% (v/v) THF;

(6) 0.1% CHA+0.1% CHX+0.2% TC+0.2% $Ag_2CO_3$ in 20% (v/v) $NH_4OH$+10% (v/v) MetOH+70% (v/v) THF;

(7) 0.1% CHA+0.1% CHX+0.2% TC+0.1% $Ag_2CO_3$ in 20% (v/v) $NH_4OH$+10% (v/v) MetOH+70% (v/v) THF;

(8) 0.1% CHA+0.1% CHX+0.2% TC+0.1% $Ag_2CO_3$+1% (w/v) PCL in 0.10% (v/v) $NH_4OH$+10% (v/v) MetOH+80% (v/v) THF;

(9) 0.4% CHA+0.2% TC in 20% (v/v) $NH_4OH$+10% (v/v) MetOH+70% (v/v) THF; or

(10) 0.2% CHA+0.2% CHX+0.2% TC in 20% (v/v) $NH_4OH$+10% (v/v) MetOH+70% (v/v) THF.

Groups of disks having a 1 mm thickness were treated for one hour with one of the above solutions. The amount of drug uptake was determined using a spectrophotometric method after extraction with alcohol. The results are shown below in Table 10.

In order to determine the bacterial adherence to the expanded PTFE soft tissue patches, six 1 cm² pieces 1 mm thick expanded PTFE soft tissue repair material from each treatment group were soaked in media containing 50% (v/v) and 50% (v/v) TSB, incubated at 37° and agitated on a shaker at 50 RPM. At each 7 day interval, the patches were removed, rinsed and placed in fresh media consisting of 50% (v/v) BAS and 50% (v/v) TSB infected with $10^5$ cfu of *Staphylococcus aureus*, which is available from the American Type Culture Collection, ATCC # 10390. After each 24 hour period of incubation at 37° and shaking at 50 RPM, the patches were removed, blotted, rinsed twice and pushed across the surface of DIE drug inactivating agar to semi quantitatively determine the number of adherent organisms. Patches with greater than 100 cfu/cm² were considered colonized. The results are shown in Table 10 below.

TABLE 10

| | SOLUTION<br>Control | μg chlorhexidine/cm² <br>0 | μg TC/cm² <br>0 | μg Total Drug/cm <br>0 | Duration of Activity (days) <br>0 |
|---|---|---|---|---|---|
| (1) | 0.4% CHA +<br>0.2% Ag₂CO₃<br>in 20% NH₄OH +<br>10% MetOH + 70% THF | 226 | — | 226 | <7 |
| (2) | 0.4% CHA +<br>0.1% Ag2CO3 +<br>1% PCL<br>in 20% NH₄OH +<br>10% MetOH + 70% THF | 373 | — | 373 | <7 |
| (3) | 0.2% CHA + 0.2% CHX +<br>0.2% Ag₂CO₃<br>in 20% NH₄OH +<br>10% MetOH + 70% THF | 307 | — | 307 | >7<14 |
| (4) | 0.2% CHA + 0.2% CHX +<br>0.1% Ag₂CO₃ +<br>1% PCL<br>in 20% NH₄OH +<br>10% MetOH + 70% THF | 400 | — | 400 | >7<14 |
| (5) | 0.2% CHA +<br>0.2% TC +<br>0.2% Ag₂CO₃<br>in 20% NH₄OH +<br>10% MetOH + 70% THF | 74 | 168 | 242 | >7<14 |
| (6) | 0.1% CHA + 0.1% CHX +<br>0.2% TC +<br>0.2% Ag₂CO₃<br>in 20% NH₄OH +<br>10% MetOH + 70% THF | 118 | 155 | 273 | <7 |
| (7) | 0.1% CHA + 0.1% CHX +<br>0.2% TC +<br>0.1% Ag₂CO₃<br>in 20% NH₄OH +<br>10% MetOH + 70% THF | 209 | 244 | 453 | >7<14 |
| (8) | 0.1% CHA + 0.1% CHX +<br>0.2% TC +<br>0.1% Ag₂CO₃<br>in 1% PCL<br>in 20% NH₄OH +<br>10% MetOH + 70% THF | 128 | 140 | 268 | >21 |
| (9) | 0.4% CHA +<br>0.2% TC +<br>in 20% NH₄OH +<br>10% MetOH + 70% THF | 433 | 158 | 591 | <7 |
| (10) | 0.2% CHA + 0.2% CHX +<br>0.2% TC +<br>in 20% NH₄OH +<br>10% MetOH + 70% THF | 515 | 215 | 730 | >7<14 |

These results demonstrate the synergistic effect of treating expanded PTFE soft tissue patches with a mixture of CHX and CHA, particularly when comparing the significant improvement in chlorhexidine retention and increased duration of efficacy for patches from groups (3), (4), and (10), when compared with groups (1), (2), and (9), respectively.

Table 10 further demonstrates the advantages of higher chlorhexidine uptake using PCL in the treatment solution of the patches of groups (2) and (4) when compared with the patches of groups (1) and (3), respectively. PCL also provides an advantage of significantly increasing duration of efficacy as evidenced by comparing the patches of group (8) with group (7), which demonstrates a three-fold increase in the duration of activity from less than 14 days to greater than 21 days despite lower total drug levels. PCL is also advantageous to use, when compared with other biodegradable polymers, because it does not affect the flexibility and softness of the resulting e-PTFE patch.

Various publications are cited herein, which are hereby incorporated by reference in their entireties.

What is claimed is:

1. An antimicrobial medical article prepared by a method comprising treating a surface of a polymeric medical article, for an effective period of time, with a solution comprising one or more solvents and an antimicrobial mixture consisting essentially of chlorhexidine free base and a water-soluble chlorhexidine salt, wherein the weight/weight ratio of chlorhexidine free base and the water-soluble chlorhexidine salt in the solution is between 1:1 and 1:5, and wherein the combined concentration of chlorhexidine free base and a water-soluble salt of chlorhexidine is about 2.00 percent (w/v) or greater.

2. The antimicrobial medical article of claim 1, wherein the concentrations of chlorhexidine free base and a water-soluble salt of chlorhexidine are each about 1.00 percent (w/v).

3. The antimicrobial medical article of claim 1, wherein the concentrations of chlorhexidine free base and a water-soluble salt of chlorhexidine are each about 1.20 percent (w/v).

4. The antimicrobial medical article of claim 1, wherein the concentrations of chlorhexidine free base and a water-soluble salt of chlorhexidine are about 0.625 percent (w/v) and about 1.375 percent (w/v), respectively.

5. The antimicrobial medical article of claim 1, wherein the concentrations of chlorhexidine free base and a water-soluble salt of chlorhexidine are each about 2.00 percent (w/v).

6. The antimicrobial medical article of claim 1, wherein the one or more solvents comprise methanol.

7. The antimicrobial medical article of claim 6, wherein the solvent is a mixture of between 75 and 95 percent (volume/volume) tetrahydrofuran and 5 and 25 percent (volume/volume) methanol.

8. The antimicrobial medical article of claim 1, wherein the one or more solvents comprise ethanol.

9. The antimicrobial medical article of claim 8, wherein the solvent is a mixture of between 10 and 30 percent (volume/volume) tetrahydrofuran and 70 and 90 percent (volume/volume) ethanol.

10. The antimicrobial medical article of claim 1, wherein the water-soluble chlorhexidine salt is chlorhexidine diacetate.

11. An antimicrobial medical article prepared by a method comprising treating a surface of a polymeric medical article, for an effective period of time, with a solution comprising one or more solvents and an antimicrobial mixture consisting essentially of chlorhexidine free base and a water-soluble chlorhexidine salt, wherein the concentrations of chlorhexidine free base and a water-soluble salt of chlorhexidine are each about 0.20 percent (w/v).

12. The antimicrobial medical article of claim 11, wherein the one or more solvents comprise methanol.

13. The antimicrobial medical article of claim 12, wherein the solvent is a mixture of between 75 and 95 percent (volume/volume) tetrahydrofuran and 5 and 25 percent (volume/volume) methanol.

14. The antimicrobial medical article of claim 11, wherein the one or more solvents comprise ethanol.

15. The antimicrobial medical article of claim 14, wherein the solvent is a mixture of between 10 and 30 percent (volume/volume) tetrahydrofuran and 70 and 90 percent (volume/volume) ethanol.

16. The antimicrobial medical article of claim 11, wherein the water-soluble chlorhexidine salt is chlorhexidine diacetate.

17. An antimicrobial medical article prepared by a method comprising treating a surface of a polymeric medical article, for an effective period of time, with a solution comprising a solvent of methanol and an antimicrobial mixture consisting essentially of a mixture of chlorhexidine free base and a water-soluble chlorhexidine salt, wherein the weight/weight ratio of chlorhexidine free base and the water-soluble chlorhexidine salt in the solution is between 1:1 and 1:5.

18. The antimicrobial medical article of claim 17, wherein the water-soluble chlorhexidine salt is chlorhexidine diacetate.

19. An antimicrobial medical article prepared by a method comprising treating a surface of a polymeric medical article, for an effective period of time, with a solution comprising one or more solvents, a silver compound, and a mixture of chlorhexidine free base and a water-soluble chlorhexidine salt, wherein the weight/weight ratio of chlorhexidine free base and the water-soluble chlorhexidine salt in the solution is between 1:1 and 1:5.

20. The antimicrobial medical article of claim 19, wherein the one or more solvents comprise methanol.

21. The antimicrobial medical article of claim 20, wherein the solvent is a mixture of between 75 and 95 percent (volume/volume) tetrahydrofuran and 5 and 25 percent (volume/volume) methanol.

22. The antimicrobial medical article of claim 19, wherein the one or more solvents comprise ethanol.

23. The antimicrobial medical article of claim 22, wherein the solvent is a mixture of between 10 and 30 percent (volume/volume) tetrahydrofuran and 70 and 90 percent (volume/volume) ethanol.

24. The antimicrobial medical article of claim 19, wherein the water-soluble chlorhexidine salt is chlorhexidine diacetate.

25. An antimicrobial medical article prepared by a method comprising treating a surface of a polymeric medical article, for an effective period of time, with a solution comprising one or more solvents and an antimicrobial mixture consisting essentially of chlorhexidine free base and a water-soluble chlorhexidine salt, wherein the weight/weight ratio of chlorhexidine free base and the water-soluble chlorhexidine salt in the solution is greater than 1:1.

26. The antimicrobial medical article of claim 25, wherein the one or more solvents comprise methanol.

27. The antimicrobial medical article of claim 26, wherein the solvent is a mixture of between 75 and 95 percent (volume/volume) tetrahydrofuran and 5 and 25 percent (volume/volume) methanol.

28. The antimicrobial medical article of claim 25, wherein the one or more solvents comprise ethanol.

29. The antimicrobial medical article of claim 28, wherein the solvent is a mixture of between 10 and 30 percent (volume/volume) tetrahydrofuran and 70 and 90 percent (volume/volume) ethanol.

30. The antimicrobial medical article of claim 25, wherein the water-soluble chlorhexidine salt is chlorhexidine diacetate.

31. The antimicrobial medical article of any one of claims 1, 11, 17, 19 or 25, wherein the article is a hydrophilic polymeric medical article.

32. The antimicrobial medical article of claim 31, wherein the article is a catheter.

33. The catheter of claim 32, wherein the catheter has a lumen which is treated, for an effective period of time, with the solution consisting essentially of one or more solvents and the mixture of chlorhexidine free base and water-soluble chlorhexidine salt.

34. The medical article of claim 31, wherein the water-soluble chlorhexidine salt is chlorhexidine diacetate.

35. The catheter of claim 32, wherein the water-soluble chlorhexidine salt is chlorhexidine diacetate.

36. The catheter of claim 33, wherein the water-soluble chlorhexidine salt is chlorhexidine diacetate.

37. An antimicrobial medical article prepared by a method comprising treating a surface of a polymeric medical article, for an effective period of time, with a solution comprising one or more solvents and an antimicrobial mixture consisting essentially of chlorhexidine free base and a water-soluble chlorhexidine salt, wherein the weight/weight ratio of chlorhexidine free base and the water-soluble chlorhexidine salt in the solution is between 1:1 and 1:5, wherein the article is a hydrophobic polymeric medical article, optionally comprising expanded polytetrafluoroethylene.

38. An antimicrobial medical article prepared by a method comprising treating a surface of a polymeric medical article, for an effective period of time, with a solution comprising (1) one or more solvents;
(2) an antimicrobial mixture consisting essentially of chlorhexidine free base and a water-soluble chlorhexidine salt; and
(3) one or more of (i) an organic acid, at a concentration of between 0.1 and 5 percent; (ii) an anti-inflammatory agent, at a concentration of between 0.1 and 5 percent; or (iii) a hydrogel at a concentration of between 0.5 to 10 percent,
wherein the weight/weight ratio of chlorhexidine free base and the water-soluble chlorhexidine salt in the solution is between 1:1 to 1:5.

39. The antimicrobial medical article of claim 38, wherein the concentration of organic acid in the solution is between 0.1 and 2 percent.

40. The antimicrobial medical article of claim 38, wherein the concentration of anti-inflammatory agent is between 0.1 and 1 percent.

41. The antimicrobial medical article of claim 38, wherein the concentration of hydrogel in the solution is between 1 and 5 percent.

42. The antimicrobial medical article of claim 38, wherein the combined concentration of the mixture of chlorhexidine free base and a water-soluble salt of chlorhexidine is about 2.00 percent (w/v) or greater.

43. The antimicrobial medical article of claim 42, wherein the concentration of organic acid in the solution is between 0.1 and 2 percent.

44. The antimicrobial medical article of claim 42, wherein the concentration of anti-inflammatory agent is between 0.1 and 1 percent.

45. The antimicrobial medical article of claim 42, wherein the concentration of hydrogel in the solution is between 1 and 5 percent.

46. The antimicrobial medical article of claim 42, and wherein the concentrations of chlorhexidine free base and a water-soluble salt of chlorhexidine are each about 0.20 percent (w/v).

47. The antimicrobial medical article of claim 46, wherein the concentration of organic acid in the solution is between 0.1 and 2 percent.

48. The antimicrobial medical article of claim 46, wherein the concentration of anti-inflammatory agent is between 0.1 and 1 percent.

49. The antimicrobial medical article of claim 46, wherein the concentration of hydrogel in the solution is between 1 and 5 percent.

50. A method of preparing a medical article comprising the steps of
(i) placing the medical article in a solution comprising
(a) a solvent comprising methanol; and
(b) an antimicrobial mixture consisting essentially of chlorhexidine free base and a water-soluble chlorhexidine salt, wherein the weight/weight ratio of chlorhexidine free base and water-soluble chlorhexidine salt in the solution is between 1:1 to 1:5;
(ii) soaking the medical article in the solution for an effective period of time to allow the medical article to swell;
(iii) removing the medical article from the solution; and
(iv) drying the medical article.

51. The method of claim 50, wherein the combined concentration of the mixture of chlorhexidine free base and a water-soluble salt of chlorhexidine is about 2.00 percent (w/v) or greater.

52. The method of claim 50, wherein the concentrations of chlorhexidine free base and a water-soluble salt of chlorhexidine are each about 0.20 percent (w/v).

53. The method of claim 51, wherein the concentrations of chlorhexidine free base and a water-soluble salt of chlorhexidine are each about 1.00 percent (w/v).

54. The method of claim 51, wherein the concentrations of chlorhexidine free base and a water-soluble salt of chlorhexidine are each about 1.20 percent (w/v).

55. The method of claim 51, wherein the concentrations of chlorhexidine free base and a water-soluble salt of chlorhexidine are about 0.625 percent (w/v) and about 1.375 percent (w/v), respectively.

56. The method of claim 51, wherein the concentrations of chlorhexidine free base and a water-soluble salt of chlorhexidine are each about 2.00 percent (w/v).

57. A method of preparing a catheter having a lumen comprising the steps of
(i) exposing the lumen of the catheter to a solution comprising
(a) a solvent comprising methanol; and
(b) an antimicrobial mixture consisting essentially of chlorhexidine free base and a water-soluble chlorhexidine salt, wherein the weight/weight ratio of chlorhexidine free base and water-soluble chlorhexidine salt in the solution is between 1:1 to 1:5;
(ii) filling the lumen of the catheter with the solution for an effective period of time to allow the lumen of the catheter to swell;
(iii) removing the solution from the lumen of the catheter; and
(iv) drying the catheter.

58. The method of claim 57, wherein the combined concentration of the mixture of chlorhexidine free base and a water soluble salt of chlorhexidine is about 2.00 percent (w/v) or greater.

59. The method of claim 58, wherein the concentrations of chlorhexidine free base and a water-soluble salt of chlorhexidine are each about 1.00 percent (w/v).

60. The method of claim 58, wherein the concentrations of chlorhexidine free base and a water-soluble salt of chlorhexidine are each about 1.20 percent (w/v).

61. The method of claim 58, wherein the concentrations of chlorhexidine free base and a water-soluble salt of chlorhexidine are about 0.625 percent (w/v) and about 1.375 percent (w/v), respectively.

62. The method of claim 58, wherein the concentrations of chlorhexidine free base and a water-soluble salt of chlorhexidine are each about 2.00 percent (w/v).

63. The method of claim 57, wherein the concentrations of chlorhexidine free base and a water-soluble salt of chlorhexidine are each about 0.20 percent (w/v).

64. An antimicrobial medical article prepared by a method comprising treating a surface of a polymeric medical article, for an effective period of time, with a solution comprising one or more solvents, a silver compound, and a mixture of chlorhexidine free base and a water-soluble chlorhexidine salt, wherein the silver compound is selected from the group consisting of silver carbonate and silver sulfadiazine, and wherein the weight/weight ratio of chlorhexidine free base and the water-soluble chlorhexidine salt in the solution is between 1:1 and 1:5.

* * * * *